US010227650B2

(12) United States Patent
Hill et al.

(10) Patent No.: US 10,227,650 B2
(45) Date of Patent: Mar. 12, 2019

(54) METHODS TO DETECT A SILENT CARRIER OF A NULL ALLELE GENOTYPE

(71) Applicant: Athena Diagnostics, Inc., Worcester, MA (US)

(72) Inventors: David A. Hill, Worcester, MA (US); Matthew Evans, Shrewsbury, MA (US); Corey D. Braastad, Southampton, MA (US)

(73) Assignee: Athena Diagnostics, Inc., Marlborough, MA (US)

( * ) Notice: Subject to any disclaimer, the term of this patent is extended or adjusted under 35 U.S.C. 154(b) by 472 days.

(21) Appl. No.: 14/941,011

(22) Filed: Nov. 13, 2015

(65) Prior Publication Data

US 2016/0153037 A1    Jun. 2, 2016

Related U.S. Application Data

(60) Provisional application No. 62/080,047, filed on Nov. 14, 2014.

(51) Int. Cl.
*C12P 19/34*    (2006.01)
*C12Q 1/6881*    (2018.01)
*C12Q 1/6883*    (2018.01)

(52) U.S. Cl.
CPC ......... *C12Q 1/6881* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS

| 6,673,541 B1 | 1/2004 | Klein et al. |
| 6,673,542 B2 | 1/2004 | Heroux et al. |
| 8,338,166 B2 | 12/2012 | Beer et al. |

(Continued)

FOREIGN PATENT DOCUMENTS

| JP | 2011-530305 | 12/2011 |
| JP | 2013-521764 | 6/2013 |

(Continued)

OTHER PUBLICATIONS

International Preliminary Report on Patentability issued in related International Patent Application No. PCT/US2015/060671, dated May 26, 2017.

(Continued)

*Primary Examiner* — Kenneth R Horlick
(74) *Attorney, Agent, or Firm* — Foley & Lardner LLP

(57) ABSTRACT

Provided herein are methods and compositions for the detection of silent carriers of chromosomal deletion alleles in a human subject using haploid cells (e.g., sperm cells or egg cells) derived from the subject. The methods provided herein comprise quantitative nucleic acid amplification reactions and determination of a ratio of a target gene to a reference gene, and indicate that a subject is a silent carrier of a null allele corresponding to the target gene if the ratio is at or below a threshold level. The methods provided herein allow for the detection of silent (2+0) carriers of SMA, where the individual has a deletion of the SMN1 gene on one chromosome 5 homolog and two or more copies of the SMN1 gene on other chromosome 5 homolog.

32 Claims, 4 Drawing Sheets

Specification includes a Sequence Listing.

(56) References Cited

U.S. PATENT DOCUMENTS

| | | |
|---|---|---|
| 8,454,906 B2 | 6/2013 | Mathies et al. |
| 8,628,923 B2 | 1/2014 | Hamilton et al. |
| 8,642,266 B2 | 2/2014 | Bergtsson et al. |
| 2009/0042737 A1 | 2/2009 | Katz et al. |
| 2010/0092973 A1 | 4/2010 | Davies et al. |
| 2011/0237445 A1 | 9/2011 | Andersson Svahn et al. |
| 2011/0244455 A1 | 10/2011 | Larson et al. |
| 2012/0165202 A1 | 6/2012 | Porreca et al. |
| 2013/0196324 A1 | 8/2013 | Larson et al. |
| 2014/0017683 A1 | 1/2014 | Yin et al. |
| 2014/0057799 A1 | 2/2014 | Johnson et al. |
| 2014/0199695 A1* | 7/2014 | Edelmann ............ C12Q 1/6883 435/6.11 |

FOREIGN PATENT DOCUMENTS

| | | |
|---|---|---|
| WO | WO 01/89788 | 11/2001 |
| WO | WO 2004/002627 A3 | 1/2004 |
| WO | WO 2004/091763 A2 | 10/2004 |
| WO | WO 2005/021151 A1 | 3/2005 |
| WO | WO 2006/040551 A2 | 4/2006 |
| WO | WO 2006/040554 A1 | 4/2006 |
| WO | WO 2006/096571 A2 | 9/2006 |
| WO | WO 2007/081385 A2 | 7/2007 |
| WO | WO 2007/089541 A2 | 8/2007 |
| WO | WO 2008/063227 A2 | 5/2008 |
| WO | WO 2012/170725 A2 | 6/2012 |
| WO | WO 2013/064896 A1 | 5/2013 |

OTHER PUBLICATIONS

International Search Report and Written Opinion issued in related International Patent Application No. PCT/US2015/06071, dated Mar. 7, 2016.

Yaron et al., "Detection of Spinal Muscalar Atrophy carriers by Nested Polymerase Chain Reaction of Single Sperm Cells," *Genetic Testing*, vol. 10, No. 1, pp. 18-23 (2006).

Abate et al., "Beating Poisson Encapsulation statistics using close-packed ordering," *Lab Chip*, vol. 9, No. 18, pp. 2628-2631 (2009) [Abstract].

Anna et al., "Formation of dispersions using "flow focusing" in microchannels," *Applied Physics Letters*, vol. 82, No. 3, pp. 364-366 (2003).

Baroud, "An Optical Toolbox for Total control of droplet microfluidics," *Lab Chip*, vol. 8, pp. 1029-1033 (2007). [Abstract].

Bigdeli et al., "A Simple Method for Encapsulating Single Cells in Alginate Microspheres Allows for Direct PCR and Whole Genome Amplification," *PLOS ONE*, 15 pages (2015).

Burlet et al., "Single-Sperm Analysis for Recurrence Risk Assessment of Spinal Muscular Atrophy," *European Journ. Of Human Genetics*, vol. 18, pp. 505-508 (2010).

Clausell-Tormos et al., "Droplet-Based Microfluidic Platforms for the Encapsulation and Screening of Mammalian Cells and Multicellular Organisms," *Chemistry & Biology*, vol. 15, pp. 427-437 (2008).

Edd et al., "Controlled Encapsulation of Single Cells into Monodisperse Picoliter Drops," *Lap Chip*, vol. 8, No. 8, pp. 1262-1264 (2008).

Eguizabal, et al., "Complete Meiosis from Human Induced Pluripotent Stem Cells," vol. 29, pp. 1186-1195 (2011).

Evans et al., "A Method to Detect Silent Carriers of Spinal Muscular Atrophy by Analysis of Human Sperm," 2 pages (2014) [Abstract].

Gomez-Curet et al., "Robust Quantification of the SMN Gene Copy Number by Real-Time TaqMan PCR," *Neurogenetics*, vol. 8, pp. 271-278 (2007).

Hahn, "Immortalization and Transformation of Human Cells," *Mol. Cells*, vol. 13, No. 3, pp. 351-361 (2002).

Hafner et al., "Isothermal Amplification and Multimerization of DNA by Bst DNA Polymerase," *Biotechniques*, 30(4):852-56, 858, 860, (2001).

Hunt, et al., "Integrated circuit/microfluidic chip to programmably trap and move cells and droplets with dielectrophoresis," *Lab Chip*, vol. 8, pp. 81-87 (2008).

Johnson et al., "Water-in-Carbon Dioxied Microemulsions: An Environment for Hydrophiles including Proteins," *Science*, vol. 271, No. 5249, pp. 624-626 (1996) [Abstract].

Kintses, et al., "Microfluidic droplets: New integrated workflows for biological experiments," *Curr. Opin. Chem. Biol.*, vol. 14, No. 5, pp. 548-555 (2010). [Abstract].

Lee et al., "Quantitative Analysis of SMN1 Gene and Estimation of SMN1 Deletion Carrier Frequency in Korean Population based on Real-Time PCR," *J. Korean Med. Sci.*, vol. 19, pp. 870-873 (2004).

Luo et al., "An Ashkenazi Jewish SMN1 Haplotype Specific to Duplication Alleles Improves Pan-Ethnic Carrier Screening for Spinal Muscular Atrophy," *Genetics in Medicine*, vol. 16, No. 2, pp. 149-156 (2014).

Macaulay et al., "Single Cell Genomics: Advances and Future Perspectives," *PLOS Genetics*, vol. 10, No. 1, pp. 9 pages (2014).

Novak, et al., "Single Cell Multiplex Gene Detection and Sequencing Using Microfluidically-Generated Agarose Emulsions," *Angew Chem. Int. Ed. Engl.*, vol. 50, No. 2, pp. 390-395 (2011).

Ogino et al., "Spinal Muscular Atrophy: Molecular Genetics and Diagnostics," *Expert Rev. Mol. Diagn.*, vol. 4, No. 1, pp. 15-29 (2004).

Pramanik et al., "Direct Detection of Insertion/Deletion Polymorphisms in an Autosomal region by Analyzing High-Density Markers in Individual Spermatozoa," *Am. J. Hum. Genet.*, vol. 71, pp. 1342-1352 (2002).

Prior et al., "Technical Standards and Guidelines for Spinal Muscular Atrophy Testing," *Genetics in Medicine*, vol. 13, No. 7, pp. 686-694 (2011).

Saiki, "Amplification of Genomic DNA," *PCR Protocols*, pp. 13-20 (1990).

Solvas, et al., "Fluorescence detection methods for microfluidic droplet platforms," *J. Vis. Exp.*, vol. 58, e3437, 7 pages (2001).

Stabley et al., "SMN1 and SMN2 copy numbers in cell lines derived from patients with spinal muscular atrophy as measured by array digital PCR," *Molecular Genetics & Genome Medicine*, vol. 3, No. 4, pp. 248-257 (2015).

Warren et al., "Transcription Factor Profiling in Individual Hematopoietic Progenitors by Digital RT-PCR," *PNAS*, vol. 103, No. 47, pp. 17807-17812 (2006).

Yaron et al., "Detection of Spinal Muscular Atrophy Carriers by Nested Polymerase Chain Reaction of Single Sperm Cells," *Genet. Testing*, vol. 10, No. 1, pp. 18-23 (2006) [Abstract].

Wharam et al., "Specific detection of DNA and RNA targets using a novel isothermal nucleic acid amplification assay based on the formation of a three-way junction structure," *Nucleic Acids Res.*, 29(11):E54-E54 (2001).

Zeng, et al., "High-Performances Single Cell Genetic Analysis Using Microfluidic Emulsion Generator Arrays," *Anal. Chem.*, vol. 82, No. 8, pp. 3183-3190 (2010).

Strom, et al., "1000 sample comparison of MLPA and RT-PCR for carrier detection and diagnostic testing for Spinal Muscular Atrophy Type 1," *Open Journal of Genetics*, vol. 3, pp. 111-114 (2013).

Maranda, et al., "Spinal Muscular Atrophy: Clinical validation of a single-tube multiplex real time PCR assay for determination of SMN1 and SMN2 copy numbers," *Clinical Biochemistry*, vol. 45, pp. 88-91 (2012).

Notice of Reasons for Rejection issued in co-pending Japanese Patent Application No. 2017-525979, dated Jun. 12, 2018.

* cited by examiner

METHODS TO DETECT A SILENT CARRIER OF A NULL ALLELE GENOTYPE

CROSS-REFERENCE TO RELATED APPLICATION

This application claims the benefit of U.S. Provisional Patent Application No. 62/080,047 filed Nov. 14, 2014, the contents of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 31, 2015, is named 103779-0672 SL.txt and is 1,984 bytes in size.

BACKGROUND OF THE INVENTION

Spinal muscular atrophy (SMA) is the second most common fatal autosomal recessive disorder after cystic fibrosis, affecting approximately 1 in 6,000 to 10,000 live births. The disorder is characterized by hypotonia, proximal muscle weakness and respiratory distress due to degeneration of motor neurons in the spinal cord. SMA is caused by mutations in the survival motor neuron 1 (SMN1) gene, which is located on chromosome 5 at 5q11.2-13.3. The majority of affected individuals exhibit loss of the SMN1 gene, either by complete gene deletion or through a gene conversion event involving the adjacent SMN2 gene. The SMN2 gene differs from the SMN1 gene by a single nucleotide (840C>T) in exon 7 and lies in an inverted orientation in cis- with the SMN1 gene on chromosome 5. At least one copy of the SMN1 gene is indispensable for normal survival of motor neurons. In contrast, both copies of the SMN2 gene are dispensable as approximately 5-10% of normal individuals lack both copies of SMN2, though in some cases, the number of SMN2 copies can modulate the clinical phenotype.

The molecular diagnosis of SMA is generally accomplished through the detection of a homozygous deletion of SMN1. More than 95% of SMA patents have a homozygous deletion of SMN1 exon 7. Carrier testing for SMA, however, is particularly challenging for several reasons. Because the SMN1 gene is highly homologous to SMN2, abnormalities in the SMN1 gene can only be detected with carefully designed allele-specific assays. Further, in about 4% of the carrier population, a chromosomal alteration places both copies of the SMN1 gene on one chromosome and zero copies on the other (i.e., silent carrier or 2+0 genotype). Gene dosage analysis can determine the copy number of SMN1 to detect carrier status in individuals that are heterozygous for the absence of SMN1, but are ineffective for detecting silent carrier genotypes, where two copies of the SMN1 gene are present on only one chromosome. In addition, because the SMN1 and SMN2 genes are separated by a long distance (800 kb) on the same chromosome, linkage analysis of the chromosomal defect is difficult.

SUMMARY OF THE INVENTION

Described herein, in certain embodiments, are methods and compositions for the detection of silent carriers of chromosomal deletion alleles in a human subject using haploid cells derived from the subject. In some embodiments, the haploid cells are gametes (e.g., sperm cells or egg cells). In particular embodiments, the methods provided herein allow for the detection of silent (2+0) carriers of SMA, where the individual has a deletion of the SMN1 gene on one chromosome 5 homolog and two or more copies of the SMN1 gene on other chromosome 5 homolog.

Provided herein, in certain embodiments, are methods for identifying a subject as a silent carrier of a target gene null allele. In some embodiments, the method involves (a) performing a plurality of nucleic acid amplification reactions, wherein each nucleic acid amplification reaction comprises a genomic DNA sample obtained from a single haploid cell from the subject, at least one pair of oligonucleotide primers for amplification of a target region of a target gene for the generation of a target gene amplification product, wherein the region amplified in the target gene amplification product is deleted in the target gene null allele, and at least one pair of oligonucleotide primers for amplification of a target region of a reference gene for the generation of a reference gene amplification product; (b) detecting the presence or absence of the target gene amplification product; (c) detecting the presence or absence of the reference gene amplification product; and (d) characterizing the subject as a carrier of the target gene null allele if the ratio of target gene amplification products to reference gene amplification products is at or below a threshold level. In some embodiments, the threshold level is between about 0.5 and about 0.8. For example, in some embodiments, the threshold level is threshold level is about 0.75 or about 0.8. In some embodiments, the ratio of target gene amplification products to reference gene amplification products in a silent carrier of a target gene null allele is approximately 0.5. The methods provided herein are typically performed on sample obtained from a mammalian subject, and particularly a human subject. In particular embodiments, the target gene for amplification is SMN1. In some embodiments, the target gene amplification product contains exon 7 of SMN1 or a portion thereof. In some embodiments, the reference gene is selected from among CFTR, GAPDH, HMBS, B2M, HPRT1, RPL13A, SDHA, TBP, UBC, YWHAZ, PRDX6, ADD1, HLA-A, RAD9A, ARHGEF7, EIF2B2, PSMD7, BCAT2, and ATP5O. In particular embodiments, the reference gene is CFTR. In some embodiments, homozygous deletion of the target gene is associated with a disease or condition. In some embodiments, disease or condition is spinal muscular atrophy (SMA).

Exemplary haploid cells for use in the methods include a naturally occurring gamete cells or induced haploid cells. In some embodiments, the haploid cell is a sperm cell or an egg cell. In some embodiments, where the haploid cell is an induced haploid cell, the haploid cell is derived from an induced pluripotent stem cell (iPSC). In some embodiments, the iPSC is generated from an adult stem cell from the subject.

In some embodiments, at least one oligonucleotide primer of the primer pair for amplification of the target region of the target gene and/or the reference gene is labeled with a detectable moiety, such as such as a radioactive moiety, a fluorescent moiety, or a dye molecule. In some embodiments, the nucleic acid amplification reaction is polymerase chain reaction (PCR) or particularly quantitative PCR. In some embodiments, each nucleic acid amplification reaction is performed in a separate well of a multiwell plate. In some embodiments, the target gene amplification product and/or the reference gene amplification product is detected with a labeled nucleic acid probe specific for the target gene amplification product.

In some embodiments, the methods provided involve a step of preparing the genomic DNA from single haploid cells. In an exemplary method, preparing the genomic DNA from single haploid cells involves: (a) sorting single haploid cells into separate reaction vessels at a concentration of one haploid cell per reaction vessel; and (b) contacting each sorted cell with a lysis buffer to release the genomic DNA from the cell. In some embodiments, the lysis buffer comprises an enzyme to assist in lysis of the haploid cell. For example, in some embodiments, the lysis buffer comprises a protease. In some embodiments, the lysis buffer comprises proteinase K. Preparation of the genomic DNA and the nucleic acid amplification reaction can be performed in the same reaction vessel or separate reaction vessels. Preparation of the genomic DNA and the nucleic acid amplification reaction in the same reaction vessel minimizes loss of genomic DNA. In some embodiments, the reaction vessel is a well of a microtiter plate, a microchip or reaction grid slide.

In some embodiments, the methods involve droplet digital PCR. In some embodiments, each haploid cell to be analyzed is first encapsulated in an microdroplet. In some embodiments, the microdroplets are dispersed in an aqueous-in-oil emulsion in a single vessel. In some embodiments, the microdroplets are sorted into individual vessels. In some embodiments, each haploid cell is lysed within the microdroplet. In some embodiments, the microdroplets containing the lysed cells are then subjected to a nucleic acid amplification reaction. In some embodiments, the nucleic acid amplification products are detected within the microdroplets. In other embodiments, the amplification products are isolated from the microdroplets and detected.

In some embodiments, the methods further involve determining the copy number of the target gene in a diploid cell from the test subject. In some embodiments, the methods further involve generating cell line from diploid cells of the test subject. In some embodiments, the methods further involve sequencing the SMN1 and/or SMN2 gene or portions thereof In some embodiments, the methods further involve generation of a report, wherein the report contains an assessment of the likelihood that the subject is a silent carrier of the target gene null allele.

Also provided herein are kits for the performing the methods described herein. In an exemplary embodiment a kit for the performance of the methods provided contains: (a) a pair of oligonucleotide primers specific to the SMN1 gene for the generation of a target gene amplification product, wherein the region amplified in the SMN1 gene amplification product is deleted in an SMN1 silent carrier, and (b) a pair of oligonucleotide primers specific to a reference gene for the generation of a reference gene amplification product that is not deleted in an SMN1 silent carrier; and (c) one or more reagents for performing a nucleic acid amplification reaction. In some embodiments, the kit comprises nucleotide triphosphates, a thermostable polymerase, and/or a suitable buffer. In some embodiments, the reference gene is selected from among CFTR, GAPDH, HMBS, B2M, HPRT1, RPL13A, SDHA, TBP, UBC, YWHAZ, PRDX6, ADD1, HLA-A, RAD9A, ARHGEF7, EIF2B2, PSMD7, BCAT2, and ATP5O. In some embodiments, the target gene amplification product comprises exon 7 of SMN1 or a portion thereof.

Also provided herein are microtiter plates for the performing the methods described herein. Exemplary microtiter plates contain a plurality of reaction vessels (e.g., wells), wherein one or more reaction vessels of the microtiter plate contain: (a) a pair of oligonucleotide primers specific to the SMN1 gene for the generation of a target gene amplification product, wherein the region amplified in the SMN1 gene amplification product is deleted in an SMN1 silent carrier; (b) a pair of oligonucleotide primers specific to a reference gene for the generation of a reference gene amplification product that is not deleted in an SMN1 silent carrier; and (c) one or more reagents for performing a nucleic acid amplification reaction. In some embodiments, the one or more reaction vessels comprises nucleotide triphosphates, a thermostable polymerase, and/or a suitable buffer. In some embodiments, the reference gene is selected from among CFTR, GAPDH, HMBS, B2M, HPRT1, RPL13A, SDHA, TBP, UBC, YWHAZ, PRDX6, ADD1, HLA-A, RAD9A, ARHGEF7, EIF2B2, PSMD7, BCAT2, and ATP5O. In some embodiments, the target gene amplification product comprises exon 7 of SMN1 or a portion thereof.

DETAILED DESCRIPTION OF THE PREFERRED EMBODIMENTS

Certain Terminology

Figure 1:
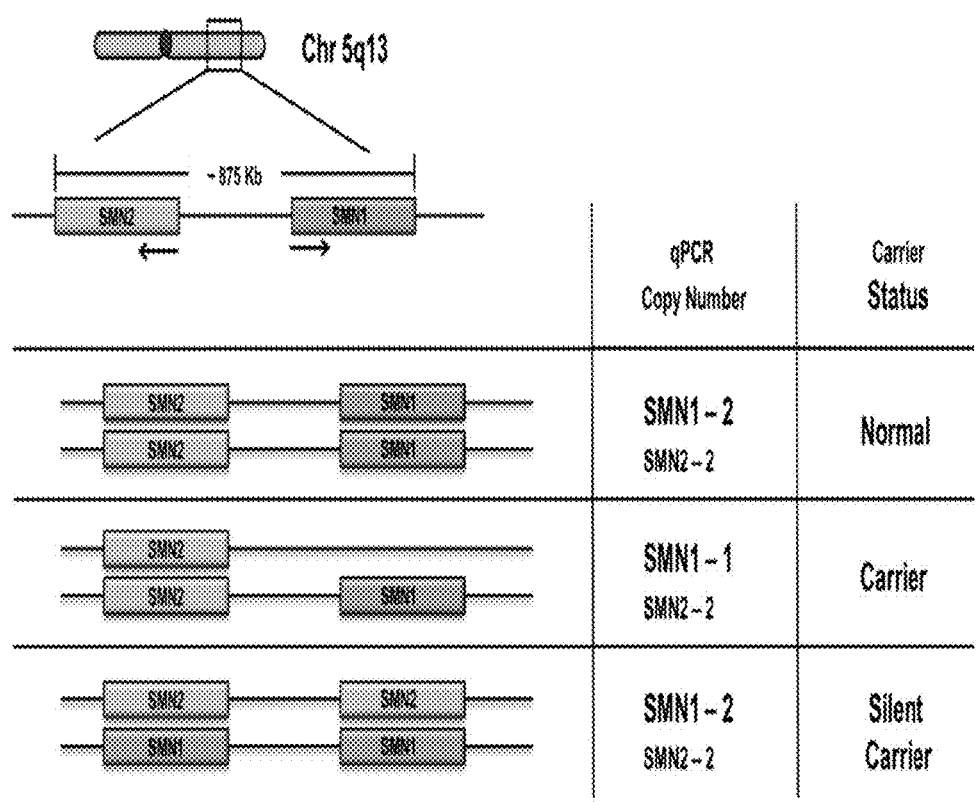
FIG. 1 illustrates the organization of SMN1 and SMN2 gene loci on chromosome 5 at 5q13. Provided are details of the chromosomal arrangement of the SMN1 and SMN2 gene copies relative to normal, carrier, and silent carrier genotypes.

To facilitate an understanding of the present disclosure, a number of terms and phrases are defined below.

As used herein, unless otherwise stated, the singular forms "a," "an," and "the" also include the plural. Thus, for example, a reference to "an oligonucleotide" includes a plurality of oligonucleotide molecules, a reference to "a label" is a reference to one or more labels, a reference to "a probe" is a reference to one or more probes, and a reference to "a nucleic acid" is a reference to one or more polynucleotides.

As used herein, unless indicated otherwise, when referring to a numerical value, the term "about" means plus or minus 10% of the enumerated value.

As used herein, a "carrier" or "genetic carrier" is an individual having at least one copy of an allele of a genetic determinant that is involved in the expression of a particular phenotype, such as SMA.

As used herein, a "silent carrier" is a genetic carrier that cannot be detected using a copy number-based diagnostic technique. For example, a "silent carrier" is a genetic carrier that has a deletion of all or part of a target gene on one chromosome homolog and two or more copies of the target gene on the other chromosome homolog.

As used herein an "SMA silent carrier" or an "SMA (2+0) carrier is a genetic carrier that has a deletion of all or part of the SMN1 gene on one chromosome 5 homolog and two or more copies of the SMN1 gene on the other chromosome 5 homolog.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplification product," also known as an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp. 13-20; Wharam et al., *Nucleic Acids Res.*, 29(11):E54-E54, 2001; Hafner et al., *Biotechniques*, 30(4):852-56, 858, 860, 2001; Zhong et al., *Biotechniques*, 30(4):852-6, 858, 860, 2001.

As used herein, the term "detecting" refers to observing a signal from a detectable label to indicate the presence of a target. More specifically, detecting is used in the context of detecting a specific sequence.

The terms "complement," "complementary" or "complementarity" as used herein with reference to polynucleotides (i.e., a sequence of nucleotides such as an oligonucleotide or a genomic nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, for the sequence 5'-A-G-T-3' is complementary to the sequence 3'-T-C-A-5'. Certain bases not commonly found in natural nucleic acids may be included in the nucleic acids of the present disclosure and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Complementarity may be "partial" in which only some of the nucleic acids' bases are matched according to the base pairing rules. Or, there may be "complete," "total," or "full" complementarity between the nucleic acids.

The term "detectable label" as used herein refers to a molecule or a compound or a group of molecules or a group of compounds associated with a probe and is used to identify the probe hybridized to a genomic nucleic acid or reference nucleic acid.

A "fragment" in the context of a polynucleotide refers to a sequence of nucleotide residues, either double- or single-stranded, which are at least about 2 nucleotides, at least about 5 nucleotides, at least about 10 nucleotides, at least about 20 nucleotides, at least about 25 nucleotides, at least about 30 nucleotides, at least about 40 nucleotides, at least about 50 nucleotides, at least about 100 nucleotides.

The terms "identity" and "identical" refer to a degree of identity between sequences. There may be partial identity or complete identity. A partially identical sequence is one that is less than 100% identical to another sequence. Partially identical sequences may have an overall identity of at least 70% or at least 75%, at least 80% or at least 85%, or at least 90% or at least 95%.

As used herein, the terms "isolated," "purified" or "substantially purified" refer to molecules, such as nucleic acid, that are removed from their natural environment, isolated or separated, and are at least 60% free, preferably 75% free, and most preferably 90% free from other components with which they are naturally associated. An isolated molecule is therefore a substantially purified molecule.

As used herein, the term "oligonucleotide" or "polynucleotide" refers to a short polymer composed of deoxyribonucleotides, ribonucleotides, or any combination thereof. Oligonucleotides are generally between about 10, 11, 12, 13, 14, 15, 20, 25, or 30 to about 150 nucleotides (nt) in length, more preferably about 10, 11, 12, 13, 14, 15, 20, 25, or 30 to about 70 nt.

As used herein, a "primer" is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal extension and/or amplification. The term "primer" includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of DNA. A "reverse primer" is complementary to the sense-strand of DNA.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the Tm of the formed hybrid.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and can occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

As used herein, an oligonucleotide is "specific" for a nucleic acid if it is capable of hybridizing to the target of interest and not substantially hybridizing to nucleic acids which are not of interest. High levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art (e.g., BLAST).

As used herein, the term "region of interest" or "target region" refers to a region of a nucleic acid to be amplified.

The term "emulsion droplet" or "emulsion microdroplet" refers to a droplet that is formed when two immiscible fluids are combined. For example, an aqueous droplet can be formed when an aqueous fluid is mixed with a non-aqueous fluid. In another example, a non-aqueous fluid can be added to an aqueous fluid to form a droplet. Droplets can be formed by various methods, including methods performed by microfluidics devices or other methods, such as injecting one fluid into another fluid, pushing or pulling liquids through an orifice or opening, forming droplets by shear force, etc. The droplets of an emulsion may have any uniform or non-uniform distribution. Any of the emulsions disclosed herein may be monodisperse (composed of droplets of at least generally uniform size), or may be polydisperse (composed of droplets of various sizes). If monodisperse, the droplets of the emulsion may vary in volume by a standard deviation that is less than about plus or minus 100%, 50%, 20%, 10%, 5%, 2%, or 1% of the average droplet volume. Droplets generated from an orifice may be monodisperse or polydisperse. An emulsion may have any suitable composition. The emulsion may be characterized by the predominant liquid compound or type of liquid compound that is used. The predominant liquid compounds in the emulsion may be water and oil. "Oil" is any liquid compound or mixture of liquid compounds that is immiscible with water and that has a high content of carbon. In some examples, oil also may have a high content of hydrogen, fluorine, silicon, oxygen, or any combination thereof, among others. For example, any of the emulsions disclosed herein may be a water-in-oil (W/O) emulsion (i.e., aqueous droplets in a continuous oil phase). The oil may be or include at least one silicone oil, mineral oil, fluorocarbon oil, vegetable oil, or a combination thereof, among others. Any other suitable components may be present in any of the emulsion phases, such as at least one surfactant, reagent, sample (i.e., partitions thereof), buffer, salt, ionic element, other additive, label, particles, or any combination thereof.

As used herein, the term "droplet" refers to a small volume of liquid, typically with a spherical shape or as a slug that fills the diameter of a microchannel, encapsulated by an immiscible fluid. The volume of a droplet, and/or the average volume of droplets in an emulsion, may be less than about one microliter (i.e., a "microdroplet") (or between about one microliter and one nanoliter or between about one microliter and one picoliter), less than about one nanoliter (or between about one nanoliter and one picoliter), or less than about one picoliter (or between about one picoliter and one femtoliter), among others. A droplet may have a diameter (or an average diameter) of less than about 1000, 100, or 10 micrometers, or of about 1000 to 10 micrometers, among others. A droplet may be spherical or nonspherical. In some embodiments, the droplet has a volume and diameter that is large enough to encapsulate a cell. In some embodiments, the droplet has a volume and diameter that is large enough to encapsulate a haploid cell. In some embodiments, the droplet has a volume and diameter that is large enough to encapsulate a sperm cell.

The term "bulk sequencing" or "next generation sequencing" or "massively parallel sequencing" refers to any high throughput sequencing technology that parallelizes the DNA sequencing process. For example, bulk sequencing methods are typically capable of producing more than one million polynucleic acid amplicons in a single assay. The terms "bulk sequencing," "massively parallel sequencing," and "next generation sequencing" refer only to general methods, not necessarily to the acquisition of greater than 1 million sequence tags in a single run. Any bulk sequencing method can be implemented in the invention, such as reversible terminator chemistry (e.g., Illumina), pyrosequencing using polony emulsion droplets (e.g., Roche), ion semiconductor sequencing (IonTorrent), single molecule sequencing (e.g., Pacific Biosciences), massively parallel signature sequencing, etc.

As used herein, the term "subject" refers to a mammal, such as a human or non-human primate, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a "subject" who possesses, or is suspected to possess, a genetic polymorphism of interest.

Overview of the Silent Carrier Genotyping Assay

Provided herein are methods for genotyping disorders where at least one chromosome of a homologous pair is lacking a gene of interest. In certain instances, the methods involve determining the carrier status for genes that have the propensity for chromosomal rearrangement that can leave one chromosome null for the gene. In certain instances, the methods involve detection of the presence or absence of that target gene of interest in a haploid cell, such as a gamete cell (e.g., a sperm or an egg cell). Because gametes are naturally haploid, the existence of a chromosome that is null for the target gene can be detected by single cell genomic analytical methods, such as by nucleic acid amplification. In some embodiments, an induced haploid cell (e.g., by induced germ cell differentiation of pluripotent stem cells) can also be employed.

Conventional genotyping is performed using diploid cells, most commonly lymphocytes (white blood cells) isolated from whole blood. Such methods are ineffective for determining the carrier status of the 2+0 silent carrier genotype because the carrier has two copies of the normal gene. Testing for genetic disorders with a single haploid cell as the source removes the complication of having two copies of all autosome genes as potential templates for analysis.

In exemplary methods, a single haploid cell is delivered to a reaction vessel and treated (e.g., lysed) to make the genomic DNA of the cell accessible for the performance of a genetic assay (e.g., PCR). In other exemplary methods, single haploid cell cells are encapsulated in microdroplets (i.e. one cell per droplet), for example, in microdroplets of an aqueous-in-oil emulsion, agarose droplet-in-oil emulsion or embedded in alginate microspheres (see, e.g., Clausell-Tormos et al. (2008) *Chem. Biol.* 15:427-437). In such embodiments, the cells are treated (e.g., lysed) within the microdroplets to make the genomic DNA of the cell accessible for the performance of a genetic assay (e.g., PCR).

In some embodiments, the assay involves nucleic acid amplification of the target gene and a reference gene that is present in the cell (e.g., a house-keeping gene) within the same reaction vessel or microdroplet, and analysis of the amplification products produced. In some embodiments a plurality of microdroplets, each containing a single cell, is contained in a single reaction vessel and a nucleic acid amplification is performed within each microdroplet. The presence or absence of the target gene with respect to the reference gene, which should always be present, is determined from multiple reactions, each reaction representing the genetic status a single haploid cell. Statistics can be used to analyze the replicate reactions to determine carrier status. In some embodiments, the amplification products are labeled. In some embodiments, the amplification products are labeled using a primer pair for amplification in which at least one primer of the primer pair is labeled with a detectable moiety. In some embodiments, the target gene amplification product and the reference gene amplification products are labeled with different detectable moieties.

In certain embodiments, a plurality of haploid cells (e.g., sperm cells) is obtained from the test subject. The haploid cells are delivered to reaction vessels at a concentration of one cell per vessel. Once sorted, each cell is individually treated to make the genomic DNA of the cell accessible for the performance of a genetic assay. In some embodiments, the genetic assay involves nucleic acid amplification of the target gene and a reference gene that is present in the cell (e.g., a house-keeping gene) in the same reaction vessel. Statistics can be used to analyze replicates reactions for the presence or absence of the target gene with respect to the reference gene, which should always be present. In such embodiments, where a plurality of haploid cells is assayed, absence of the target gene in approximately 50% of the cells from the individual indicates that the individual is a carrier of the null deletion mutation.

In alternative embodiments, a plurality of haploid cells (e.g., sperm cells) is obtained from the test subject, and the haploid cells are encapsulated into microdroplets at a concentration of one cell per microdroplet. The microdroplets can be sorted into reaction vessels at a concentration of one cell per vessel or plurality of microdroplets can be contained in a one or more vessels in an aqueous-in-oil emulsion. In some embodiments, in order to enrich to microdroplets that contain a cell, the microdroplets are sorted based on whether the microdroplet contains cell. In some embodiments, the cells are labeled. The microdroplets, each containing a haploid cell, is treated to make the genomic DNA of the cell accessible for the performance of a genetic assay. In some embodiments, the genetic assay involves nucleic acid amplification of the target gene and a reference gene that is present in the cell (e.g., a house-keeping gene) in the same microdroplet. The amplification products can be analyzed by detection of the amplification products in each of the microdroplets. In some embodiments, a microfluidic detection apparatus is employed to scan the droplets for the target gene and reference gene amplification products. Statistics can be used to analyze replicates reactions for the presence or absence of the target gene with respect to the reference gene, which should always be present. In such embodiments, where a plurality of haploid cells is assayed, absence of the target gene in approximately 50% of the cells from the individual indicates that the individual is a carrier of the null deletion mutation. Exemplary methods for the microdroplet-based emulsion amplification and detection from single cells are known and can be employed in combination with the haploid cell amplification methods provided herein (see, e.g., U.S. Pat. Nos. 8,338,166, 8,454,906, Novak et al. (2011) *Angew Chem Int Ed Engl.* 50(2): 390-395, Clausell-Tormos et al. (2008) *Chem. Biol.* 15:427-437, Novake et al. (2010) *Anal Chem.* 82(8):3183-90, and Solvas et al. (2001) *J. Vis. Exp.* (58): e3437).

As described herein, the methods provided are useful for the detection of the SMN1 silent carrier genotype of SMA in which two copies of the SMN1 gene are located on a single chromosome 5 and no copies of the gene are located on the chromosome 5 homolog. In certain embodiments, a plurality of haploid cells is obtained from the test subject suspected of having SMA. In such cases, single haploid cells obtained from the subject are delivered to reaction vessels at a concentration of one cell per vessel. Each cell is individually treated to make the genomic DNA of the cell accessible for the performance of a genetic assay for the detection of the SMN1 gene. In some embodiments, the genetic assay involves nucleic acid amplification of a target region of the SMN1 gene and a target region of a reference gene that is present in the cell (e.g., a house-keeping gene) in the same reaction vessel. Statistics can be used to analyze replicates reactions for the presence or absence of the SMN1 gene with respect to the reference gene, which should always be present. In such embodiments, where a plurality of haploid cells is assayed, absence of the SMN1 gene in approximately 50% of the cells from the individual indicates that the individual is a carrier of the SMN1 null deletion mutation.

In alternative embodiments for detection of an individual as a carrier of the SMN1 null deletion mutation, a plurality of haploid cells (e.g., sperm cells) is obtained from the test subject, and the haploid cells are encapsulated into microdroplets at a concentration of one cell per microdroplet. The microdroplets can be sorted into reaction vessels at a concentration of one cell per vessel or plurality of microdroplets can be contained in a one or more vessels in an aqueous-in-oil emulsion. In some embodiments, in order to enrich to microdroplets that contain a cell, the microdroplets are sorted based on whether the microdroplet contains cell. In some embodiments, the cells are labeled. The microdroplets, each containing a haploid cell, is treated to make the genomic DNA of the cell accessible for the performance of a genetic assay for the detection of the SMN1 gene. In some embodiments, the genetic assay involves nucleic acid amplification of a target region of the SMN1 gene and a reference gene that is present in the cell (e.g., a house-keeping gene) in the same microdroplet. The amplification products can be analyzed by detection of the amplification products in each of the microdroplets. In some embodiments, a microfluidic detection apparatus is employed to scan the droplets for the target gene and reference gene amplification products. Statistics can be used to analyze replicates reactions for the presence or absence of the SMN1 gene with respect to the reference gene, which should always be present. In such embodiments, where a plurality of haploid cells is assayed, absence of the SMN1 gene in approximately 50% of the cells from the individual indicates that the individual is a carrier of the null deletion mutation. Exemplary methods for the microdroplet-based emulsion amplification and detection from single cells are known and can be employed in combination with the haploid cell amplification methods provided herein for detection of the SMN1 null deletion mutation and silent carrier status (see, e.g., U.S. Pat. Nos. 8,338,166, 8,454,906, Novak et al. (2011) *Angew Chem Int Ed Engl.* 50(2): 390-395, Clausell-Tormos et al. (2008) *Chem. Biol.* 15:427-437, Novake et al. (2010) *Anal Chem.* 82(8):3183-90, and Solvas et al. (2001) *J. Vis. Exp.* (58): e3437).

In some embodiments, the assay further involves analysis of the gene copy number in diploid cells of the test subject.

In some embodiments, genetic analysis of single diploid cells from the test subject is performed to determine the copy number of the SMN1 and/or SMN2 genes. In some embodiments, genetic analysis of single diploid cells from the test subject is performed to confirm that the subject has two copies of the SMN1 gene. In some embodiments, an assay to determine gene copy number of the SMN1 gene is performed as described in Curet et al. (2007) *Neurogenetics* 8:271-278. In some embodiments, the diploid cells are blood cells.

In some embodiments, the assay further involves generation of cell lines from diploid cells (e.g. from lymphocytes, fibroblasts, stem cells, epithelial cells, etc.) of the test subject. In some embodiments, cell lines are generated using standard techniques for cell transformation (e.g., Hahn (2002) *Mol. Cells* 13(3):351-361; Stabley et al. (2015) Mol. Gen. Genomic Med. 3(4) 248-257). In some embodiments, the transformed cell lines are employed for analysis of gene copy number of the SMN1 and/or SMN2 genes. In some embodiments, genetic analysis of the transformed cell lines is performed to confirm that the subject has two copies of the SMN1 gene.

In some embodiments, the assay further involves generation of cell lines from diploid cells of the test subject identified as having a SMN1 gene silent carrier genotype. Generation of cell lines provides a long term record of an individual with this rare genotype. An immortal cell line provides an unlimited volume of sample from such an individual without any additional sample draws. Such cells lines can be employed to identify sequence markers unique to "silent carrier" founder alleles.

In some embodiments, the methods further comprise sequencing of the target genes, e.g., SMN1 and SMN2 genes, or one or more portions thereof. In some embodiments, the target gene amplification products are sequenced. In some embodiments, the target gene amplification products generated by PCR in aqueous-oil microdroplets are sequenced. Any suitable method for sequencing nucleic acids can be employed. In some embodiments, next generation sequencing is employed.

In some embodiments, the methods further involve the generation of a report based on the results of the assay. In some embodiments, the methods further involve determining the risk of producing offspring with SMA based on the results of the assay.

Target and Reference Genes

The methods described herein can be employed for the detection of a null deletion in a target gene. In particular embodiments, the target gene is one where at least one copy of the gene is deleted on one chromosome and present in multiple copies (e.g., 2, 3, 4 or more copies) on the homologous chromosome or other location(s) in a silent carrier. In particular embodiments, the target gene is the SMN1 gene.

For practice of the methods provided herein, the absence of the target gene is determined by the absence of a nucleic acid amplification product relative to a reference nucleic acid amplification product from a selected reference gene, where the target gene and the reference gene are amplified in the same reaction vessel. Exemplary reference genes for use in the methods provided include, but are not limited to, cystic fibrosis transmembrane transregulator (CFTR), Glyceraldehyde-3-phosphate dehydrogenase (GAPDH), Beta-2-microglobulin (B2M), Hydroxymethyl-bilane synthase (HMBS), Hypoxanthine phosphoribosyl-transferase 1 (HPRT1), Ribosomal protein L13a (RPL13A), Succinate dehydrogenase complex, subunit A (SDHA), TATA box binding protein (TBP), Ubiquitin C (UBC), Tyrosine 3-monooxygenase/tryptophan 5-monooxygenase binding to phosphorylated activation protein, zeta polypeptide (YWHAZ), peroxiredoxin-6 (PRDX6), Alpha-adducin (ADD1), Major Histocompatibility Complex, Class I, A (HLA-A), RAD9A, Rho Guanine Nucleotide Exchange Factor (GEF) 7 (ARHGEF7), Eukaryotic Translation Initiation Factor 2B, Subunit 2 Beta (EIF2B2), 26S Proteasome Non-ATPase Regulatory Subunit 7 (PSMD7), Branched Chain Amino-Acid Transaminase 2 (BCAT2), and ATP Synthase Subunit O (ATP5O). In particular embodiments, the reference gene for use in the methods provided herein is the CFTR gene.

Subjects for Testing and Sample Acquisition

Generally, the methods provided herein are employed to determine the silent carrier status in a mammal (e.g., primate, rabbit, dog, cat, sheep and pig). In particular embodiments, the subject is a human patient.

In certain instances, selection of subjects for testing for silent carrier status for a particular target gene is based on multiple factors. In some embodiments, the subject is selected for testing based on the prevalence of the deletion in the general population or a particular ethnic group. In some embodiments, the subject is selected for testing based on a confirmed or suspected family history of a disease associated with the target gene. In some embodiments, the subject is selected for testing based on a confirmed or suspected family history of SMA. In certain instances, a subject is selected for testing for silent carrier status based on the recommendation of a licensed physician or as a part of a genetic counseling procedure or program.

In certain instances, a subject selected for testing is suspected of having a deletion a deletion of the SMN1 gene on one chromosome 5 homolog and two or more copies of the SMN1 gene on the other chromosome 5 homolog.

In particular embodiments, natural haploid cells are employed in the assay. In such instances, standard methods for obtaining male or female gametes as appropriate for the particular subject can be employed.

In particular embodiments, induced haploid cells derived from adult stem cells are employed in the assay. In such instances, any source of stem cells from the subject can be used. Adult stem cells can be obtained from a variety of organs and tissues, including, but not limited to brain, bone marrow, peripheral blood, blood vessels, skeletal muscle, skin, teeth, heart, gut, liver, ovarian epithelium, and testis. In certain instances, the adult stem cells are treated to induce pluripotency of the stem cells (e.g., generate an induced pluripotent stem cell (iPSC)). For example, in certain instances, adult stem cells can be modified to express one or more genes that induce pluripotency, such as, for example, Oct4, Sox2, cMyc, and/or Klf4. Once a pluripotent cell is generated, the cell can be treated to induce meiosis to generate an induced haploid cell (see, e.g., Eguizabal et al. (2011) *Stem Cells* 29:1186-1195).

Single Cell Sorting Methods

Any suitable method for sorting individual haploid cells into separate reaction vessels for analysis can be used in the methods provided. Exemplary cell sorting methods include, but are not limited to, dilution sorting, droplet based microfluidics, flow cytometry, fluorescence activated cell sorting (FACS), magnetic activated cell sorting (MACS), laser-assisted cell picking, micropatterning on controlled patches of extracellular matrix (ECM) or other ligands or microfluidic chip sorting. In some embodiments, the cells are seeded into a reaction vessel at a concentration of one cell per well. Methods for sorting of single cells and seeding of single cells into a variety of reaction vessels for genomic analysis are known in the art and include, for example, methods as described in U.S. Pat. No. 6,673,542 and U.S. Patent Pub. No. 2011/0237445.

In certain embodiments, the haploid cells are labeled with a suitable dye (e.g., Hoechst 33342) to assist the haploid cell sorting method. In such methods, the haploid cells are contacted with the dye for a predetermined length of time to allow for labeling of the haploid cells. The labeled haploid cells are then subjected to the selected cell sorting method.

Cells can be sorted into any suitable reaction vessel appropriate for performance of the methods provided herein. In some embodiments, the cells are sorted in a suitable reaction vessel appropriate for the hybridization of a gene-specific probe. In some embodiments, the cells are sorted in a suitable reaction vessel appropriate for nucleic acid amplification. Exemplary reaction vessels include, but are not limited to, multiwell plates, microtiter plates, reaction grid slides (e.g., AmpliGrid slides and chemically structured glass slides containing hydrophilic anchor spots each framed by a hydrophobic ring) and PCR tubes. In particular embodiments, the single cells are sorted into a multiwell plate such as a 96-, 384-, 1536- or greater multiwell plate. In some embodiments, the placement of single cells into the reaction vessels is confirmed by visual or automated inspection under a microscope. In some embodiments, the placement of single cells into the reaction vessels is confirmed by addition of cell specific dye or probe. In some embodiments, the single haploid cells are labeled prior to cell sorting and confirmation of cell sorting is confirmed by detection of the labeled cells. For example, in some embodiments, detection of the strength of the signal, such as fluorescent signal, is indicative the number of cells per well.

In some embodiments, the cells are seeded into reaction vessels at a concentration of a single cell per reaction vessel for lysis of the cells, and the nucleic acid amplification reaction is performed in the same reaction vessel. In some embodiments, the cells are seeded into reaction vessels at a concentration of a single cell per reaction vessel for lysis of the cells, and the nucleic acid amplification reaction is performed in a different reaction vessel (i.e., the genomic DNA sample is transferred to a new reaction vessel for the nucleic acid amplification reaction).

In some embodiments, the cells are encapsulated individually in microdroplets. A microdroplet generally includes an amount of a first sample fluid in a second carrier fluid. Any technique known in the art for forming droplets may be used with methods of the invention. An exemplary method involves flowing a stream of the sample fluid containing the target material (e.g., a haploid cell) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material. The carrier fluid may be any fluid that is immiscible with the sample fluid. An exemplary carrier fluid is oil. In certain embodiments, the carrier fluid includes a surfactant.

In some embodiments, a microfluidic device is used to generate single cell emulsion droplets. The microfluidic device ejects single cells in aqueous reaction buffer into a hydrophobic oil mixture. The device can create thousands of emulsion microdroplets per minute. After the emulsion microdroplets are created, the device ejects the emulsion mixture into a trough. The mixture can be pipetted or collected into a standard reaction tube for lysis and/or thermocycling. In some embodiments the microdroplets are seeded into individual reaction vessels (e.g. a microtiter plate, a microchip or reaction grid slide).

In some embodiments, the microdroplets are sorted to enrich for microdroplets carrying a single haploid cell. In some embodiments, the microdroplets carrying single haploid cells are sorted based on differences the light refractory properties of the microdroplets carrying single haploid cells from empty microdroplets and/or microdroplets carrying more than one haploid cell. In some embodiments, the haploid cells are labeled with a suitable dye (e.g., Hoechst 33342) to assist the cell sorting method. In such methods, the haploid ells are contacted with the dye for a predetermined length of time to allow for labeling of the haploid cells. The microdroplets carrying labeled haploid cells are then subjected to the selected cell sorting method.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of the droplets does not vary by more than plus or minus 5% of the average size of the droplets. In some cases, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Microfluidic systems and devices have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227.

Custom microfluidics devices for single-cell analysis are routinely manufactured in academic and commercial laboratories (Kintses et al. (2010) *Current Opinion in Chemical Biology* 14:548-555). For example, chips may be fabricated from polydimethylsiloxane (PDMS), plastic, glass, or quartz. In some embodiments, fluid moves through the chips through the action of a pressure or syringe pump. Single cells can even be manipulated on programmable microfluidic chips using a custom dielectrophoresis device (Hunt et al. (2008) *Lab Chip* 8:81-87). In one embodiment, a pressure-based PDMS chip comprised of flow-focusing geometry manufactured with soft lithographic technology is used (Dolomite Microfluidics (Royston, UK)) (Anna et al. (2003) *Applied Physics Letters* 82:364-366). The stock design can typically generate 10,000 aqueous-in-oil microdroplets per second at size ranges from 10-150 μm in diameter. In some embodiments, the hydrophobic phase will consist of fluorinated oil containing an ammonium salt of carboxy-perfluoropolyether, which ensures optimal conditions for molecular biology and decreases the probability of droplet coalescence (Johnston et al. (1996) *Science* 271:624-626). To measure periodicity of cell and droplet flow, images can be recorded at 50,000 frames per second using standard techniques, such as a Phantom V7 camera or Fastec InLine (Abate et al. (2009) *Lab Chip* 9:2628-31).

The microfluidic system can optimize microdroplet size, input cell density, chip design, and cell loading parameters such that greater than 98% of droplets contain a single cell. Three common methods for achieving such statistics are: (i) extreme dilution of the cell solution; (ii) fluorescent selection of droplets containing single cells; and (iii) optimization of cell input periodicity. For each method, the metrics for success include: (i) encapsulation rate (i.e., the number of drops containing exactly one cell); (ii) the yield (i.e., the fraction of the original cell population ending up in a drop containing exactly one cell); (iii) the multi-hit rate (i.e., the fraction of drops containing more than one cell); (iv) the negative rate (i.e., the fraction of drops containing no cells); and (v) encapsulation rate per second (i.e., the number of droplets containing single cells formed per second).

In some embodiments, single cell emulsions are generated by extreme cell dilution. Under disordered conditions, the probability that a microdroplet will contain k cells is given by the Poisson distribution:

$$f(k;\lambda)=(\lambda^k e^{-\lambda})/k!,$$

where e is the natural logarithm and the expected number of occurrences in the interval is $\lambda$. Thus, for $P(k=1) \approx 0.98$, the cell solution must be extremely dilute, such that $\lambda$ 0.04 and only 3.84% of all drops contain a single cell.

In some embodiments, a simple microfluidic chip with a drop-making junction is used, such that an aqueous stream flows through a 10 µm square nozzle and dispenses the aqueous-in-oil emulsion mixtures into a reservoir. The emulsion mixture can then be pipetted from the reservoir and thermocycled in standard reaction tubes, microtiter plates, microchips or reaction grid slides. This method will produce predictably high encapsulation rates and low multi-hit rates, but a low encapsulation rate per second. A design that can achieve filled droplet throughput of 1000 Hz is capable of sorting up to $10^6$ cells in less than 17 minutes.

In some embodiments, fluorescence techniques can also be used to sort microdroplets with particular emission characteristics (Baroud et al. (2007) *Lab Chip* 7:1029-1033; Kintses et al. (2010) *Current Opinion in Chemical Biology* 14:548-555). In these studies, chemical methods are used to stain cells. In some embodiments, autofluorescence is used to select microdroplets that contain cells. A fluorescent detector reduces the negative rate resulting from extreme cell dilution. A microfluidic device can also be equipped with a laser directed at a "Y" sorting junction downstream of the cell encapsulation junction. The Y junction has a "keep" and a "waste" channel. A photomultiplier tube is used to collect the fluorescence of each drop as it passes the laser. The voltage difference is calibrated between empty drops and drops with at least one cell. Next, when the device detects a droplet that contains at least one cell, and electrodes at the Y sorting junction create a field gradient by dielectrophoresis (Hunt et al. (2008) *Lab on a Chip* 8:81-87) and push droplets containing cells in to the keep channel. The microfluidic device uses extreme cell dilution to control the multi-hit rate and fluorescent cell sorting to reduce the negative rate.

In some embodiments, input cell flow is aligned with droplet formation periodicity, such that greater than 98% of droplets contain a single cell (Edd et al. (2008) *Lab Chip* 8:1262-1264; Abate et al. (2009) *Lab Chip* 9:2628-31). In these microfluidic devices, a high-density suspension of cells is forced through a high aspect-ratio channel, such that the cell diameter is a large fraction of the channel's width. The chip is designed with a 27 µm×52 µm rectangular microchannel that flows cells into microdroplets at >104/min (Edd et al. (2008) *Lab Chip* 8:1262-1264). A number of input channel widths and flow rates are tested to arrive at an optimal solution.

In some embodiments, cells with different morphology behave differently in the microchannel stream of the microfluidic device, confounding optimization of the technique when applied to clinical biological samples. To address this issue, in some embodiments, a field gradient perpendicular to the microchannel by dielectrophoresis is induced. Dielectrophoresis pulls the cells to one side of the microchannel, creating in-channel ordering that is independent of cell morphology. This method requires substantial optimization of charge and flow rate and a more complicated chip and device design, so this method may be necessary if existing methodologies fail to perform for certain cell types.

In some embodiments, the methods of the invention use single cells in reaction containers, rather than emulsion droplets. Examples of such reaction containers include 96 well plates, 0.2 mL tubes, 0.5 mL tubes, 1.5 mL tubes, 384-well plates, 1536-well plates, etc.

Preparation of Genomic DNA

Preparation of a genomic DNA sample from haploid cells for a genetic assay, such as nucleic acid amplification, typically involves lysis of the cells to expose the genomic DNA. Any suitable lysis buffer for the preparation of genomic DNA from cells can be used. In certain instances, particular haploid cells, such as sperm cells, are resistant to conventional lysis procedures. Accordingly, in certain embodiments, the methods for preparation of a genomic DNA sample involve lysis of the cells using one or more suitable enzymes (e.g. a protease, such as proteinase K).

In some embodiments, the haploid cells are lysed in an alkaline lysis solution (e.g. a potassium hydroxide alkaline lysis solution) or detergent solution, e.g. Tween 20. In some embodiments, the lysis solution contains enzyme to assist in lysis, such as, for example, a protease (e.g., proteinase K). In some embodiments, the lysis solution also contains one or more additional components, such as a redox stabilization reagent (e.g., dithiothreitol (DDT)), a chelating agent (e.g., EDTA) or a buffering agent.

In some embodiments, where the haploid cells are encapsulated in microdroplets, the lysis buffer is introduce at the time of cell encapsulation using a co-flow drop maker to prevent premature rupture of the cells.

Nucleic Acid Amplification and Detection

Following preparation of the genomic DNA, a genetic assay is performed to detect the target gene null allele. In particular embodiments of the methods provided, the target gene null allele is detected by nucleic acid amplification, for example, by polymerase chain reaction (PCR). In some embodiments, the region that overlaps or contains the deletion in the target gene is amplified from the genomic DNA sample from the single haploid cell from the subject. In samples that have the deletion, the target gene region will not be amplified. To ensure that the genomic DNA sample was present in the reaction vessel and that the conditions for nucleic acid amplification were suitable, a reference gene is also amplified in the same amplification reaction as the target gene. Accordingly, success or failure of the target gene amplification is assessed relative to the amplification of the reference gene.

For any particular subject that is a silent carrier for the target gene null allele, approximately 50% of the haploid cells produced by the subject will have the null allele.

Accordingly, 50% of the haploid cells tested from the subject using the methods provided herein will fail to amplify the target gene relative to the reference gene, indicating that the target gene has the deletion in the haploid cell. Accordingly, multiple amplification reactions are performed (i.e., multiple haploid cells from the subject tested) in order to confirm that the deletion is present. In some embodiments 10, 20, 30, 40, 50, 60, 70, 80, 90, 100, 150, 200, 250, 500, 1000, 5000 or more amplification reactions are performed, where each amplification reaction represents a single haploid cell.

Exemplary reaction vessels for nucleic acid amplification include, but are not limited to, multiwell plates, microtiter plates, microchips, reaction grid slides (e.g., AmpliGrid slides and chemically structured glass slides containing hydrophilic anchor spots each framed by a hydrophobic ring) and PCR tubes.

Exemplary nucleic acid amplification reaction mixtures for the practice of the methods contain a DNA template (e.g., a genomic DNA sample obtained from a single haploid cell), at least one oligonucleotide primer set specific for a target gene (e.g., for amplification of a target region of a target gene), at least one oligonucleotide primer set specific for a reference gene (e.g., for amplification of a target region of the reference gene), a thermostable DNA polymerase, deoxynucleoside triphosphates (dNTPs), $Mg^{2+}$, and a suitable buffer.

In exemplary embodiments, the amplification reaction mixture comprises about, more than about, or less than about 1, 5, 10, 15, 20, 30, 50, 100, or 200 mM Tris. In some embodiments, the amplification reaction mixture comprises potassium chloride at a concentration about, more than about, or less than about 10, 20, 30, 40, 50, 60, 80, 100, 200 mM. In some embodiments, the amplification reaction mixture comprises about 15 mM Tris and 50 mM KCl. In some embodiments, the amplification reaction mixture comprises deoxyribonucleotide triphosphate molecules, including dATP, dCTP, dGTP, dTTP, in concentrations of about, more than about, or less than about 50, 100, 200, 300, 400, 500, 600, or 700 μM each. In some embodiments, magnesium chloride or magnesium acetate ($MgCl_2$) is added to the amplification reaction mixture at a concentration of about, more than about, or less than about 1.0, 2.0, 3.0, 4.0, or 5.0 mM. In some embodiments, the amplification reaction mixture comprises $MgCl_2$ at a concentration about 3.2 mM. In some embodiments, the amplification reaction mixture comprises magnesium acetate or magnesium is used. In some embodiments, magnesium sulfate. In some embodiments, the amplification reaction mixture comprises a non-specific blocking agent, such as BSA or gelatin from bovine skin, wherein the gelatin or BSA is present in a concentration range of approximately 0.1-0.9% w/v. Other possible blocking agents can include betalactoglobulin, casein, dry milk, or other common blocking agents. In some cases, preferred concentrations of BSA and gelatin are about 0.1% w/v Exemplary polymerase enzymes for nucleic acid amplification include, but are not limited to, thermostable DNA polymerases, such as *Thermus thermophilus* (Tth) DNA polymerase, *Thermus aquaticus* (Taq) DNA polymerase, *Thermotoga neopalitana* (Tne) DNA polymerase, *Thermotoga maritima* (Tma) DNA polymerase, *Thermococcus litoralis* (Tli or VENT™) DNA polymerase, *Thermus eggertssonii* (Teg) DNA polymerase, *Pyrococcus furiosus* (Pfu) DNA polymerase, DEEPVENT. DNA polymerase, *Pyrococcus woosii* (Pwo) DNA polymerase, *Pyrococcus* sp KDD2 (KOD) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME) DNA polymerase, *Methanobacterium thermoautotrophicum* (Mth) DNA polymerase, *mycobacterium* DNA polymerase (Mtb, Mlep), or mutants, variants or derivatives thereof. In some embodiments, the polymerase is a hot-start polymerase, such as a hot start Taq polymerase. In some embodiments, the polymerase is a chemically modified hot-start polymerase or an antibody modified hot start polymerase.

Standard methods for nucleic acid amplification of nucleic acid from genomic DNA obtained from a single cell are known in the art and can be employed in the methods provided herein (see, e.g., U.S. Patent Pub. No. 2011/0237445). In an exemplary protocol, nucleic acid amplification comprises, in general steps, (a) contacting each nucleic acid strand template with four different nucleotide triphosphates and one oligonucleotide primer pair for each different specific sequence being amplified, wherein each primer of the primer pair is selected to be substantially complementary to different strands of each specific sequence, such that the extension product synthesized from one primer, when it is separated from its complement, can serve as a template for synthesis of the extension product of the other primer, said contacting being at a temperature which promotes hybridization of each primer to its complementary nucleic acid strand; (b) contacting each nucleic acid strand, at the same time as or after step (a), with a thermostable DNA polymerase such as from *Thermus aquaticus* which enables combination of the nucleotide triphosphates to form primer extension products complementary to each strand of each nucleic acid; (c) maintaining the mixture from step (b) at an effective temperature for an effective time to promote the activity of the enzyme, and to synthesize, for each different sequence being amplified, an extension product of each primer which is complementary to each nucleic acid strand template, but not so high as to separate each extension product from its complementary strand template; (d) heating the mixture from step (c) for an effective time and at an effective temperature to separate the primer extension products from the templates on which they were synthesized to produce single-stranded molecules, but not so high as to irreversibly denature the enzyme; (e) cooling the mixture from step (d) for an effective time and to an effective temperature to promote hybridization of each primer to each of the single-stranded molecules produced in step (d); and (f) maintaining the mixture from step (e) at an effective temperature for an effective time to promote the activity of the enzyme and to synthesize, for each different sequence being amplified, an extension product of each primer which is complementary to each nucleic acid strand template produced in step (d), but not so high as to separate each extension product from its complementary strand template wherein the effective time and temperatures in steps (e) and (f) may coincide (steps (e) and (f) are carried out simultaneously), or may be separate. Steps (d)-(f) may be repeated until the desired level of sequence amplification is obtained.

In some embodiments, where the lysed haploid cells are encapsulated in microdroplets, the amplification reaction mixture is introduced by dilution of the microdroplets by droplet merger and/or droplet picoinjection of the amplification reagents.

In some embodiments, the amplification reaction is carried out in microdroplets by performing digital PCR, such as microfluidic-based digital PCR or droplet digital PCR. In some embodiments, thermal cycling is accomplished in a single vessel (e.g. tube, microtiter well, a microchip or reaction grid slide) containing a plurality of microdroplets or as a continuous flow of the microdroplets through a microfluidic channel through defined temperature zones (see, e.g., US Patent Pub. 2009/0042737).

In some cases, a target region for amplification is about, more than about, or less than about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some cases, a target for amplification is about 10 to about 100, about 100 to about 200, about 100 to about 300, about 100 to about 400, about 100 to about 500, about 100 to about 600, about 100 to about 700, about 100 to about 800, about 100 to about 900, about 100 to about 1000, about 1000 to about 2000, about 1000 to about 5000, or about 1000 to about 10,000 bases or base-pairs in length.

The length of the forward primer and the reverse primer can depend on the sequence of the target polynucleotide and the target locus. For example, the length and/or Tm of the forward primer and reverse primer can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some cases, a primer is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

In some embodiments, primers for amplification within the amplification reaction mixture can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 µM. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 µM. The concentration of primers can be about 0.5 µM. Amenable ranges for target nucleic acid concentrations in PCR are between about 1 pg and about 500 ng In an exemplary assay according to methods provided herein, the nucleic acid amplification reaction contains an oligonucleotide primer pair that is an oligonucleotide primer set for amplification of a target region of the target gene (e.g., exon 7 of SMN1 or a portion thereof) and an oligonucleotide primer set specific for the reference gene. Exemplary primers for the amplification of a target gene (e.g., an SMN1 target gene) and a reference gene (e.g., a CFTR reference gene) are provided. In some embodiments, for amplification of the target region of SMN1, at least one of the primers of the primer pairs distinguishes between SMN1 and SMN2. SMN1 and SMN2 differ by a single nucleotide difference (C/T) at position 6 in exon 7 of SMN1 and SMN2. In some embodiments, the allele specific primer is a forward primer distinguishes between SMN1 and SMN2, having a C or T, respectively, at the 3' end of the primer corresponding to position 6 in exon 7 of SMN1 and SMN2. In some embodiments, a mismatch T→G also added at the −3 position from the 3' end of both SMN1 and SMN2 forward primers which aids in allele specificity.

In some embodiments, the forward primer for amplification of the target region of SMN1 has the sequence SEQ ID NO: 1. In some embodiments, the reverse primer for amplification of the target region of SMN1 has the sequence SEQ ID NO: 3. In some embodiments, the forward primer for amplification of the target region of SMN2 has the sequence SEQ ID NO: 2. In some embodiments, the reverse primer for amplification of the target region of SMN2 has the sequence SEQ ID NO: 3.

In some embodiments, the forward primer for amplification of a CFTR reference gene has the sequence SEQ ID NO: 4. In some embodiments, the reverse primer for amplification of a CFTR reference gene has the sequence SEQ ID NO: 5.

In some embodiments, one or more oligonucleotide primers in the nucleic acid amplification reaction are labeled. In some embodiments, the oligonucleotide primers are labeled with a detectable moiety, such as a radioactive moiety, a fluorescent moiety, or a dye molecule. In some embodiments, the composition comprises a dual labeled fluorescence energy transfer (FRET) probe. In particular embodiments, at least one primer of the oligonucleotide primer set specific for the target gene and at least one primer of the oligonucleotide primer set specific for the reference gene is labeled.

In some embodiments, the presence or absence of the target gene and reference gene amplification products are detected following the nucleic acid amplification reaction. Any suitable method for the detection of an amplification product, such as by gel electrophoresis or labeled nucleic acid probes, can be employed.

In some embodiments, a quantitative PCR method is employed to monitor the amplification of target gene and the reference gene in each nucleic acid reaction (e.g. a comparative Ct method). In such methods, at least one oligonucleotide primer of each primer pair specific for the target gene or the reference gene is labeled with a different detectable moiety, which allows detection of the different amplification products within the same reaction vessel.

In particular embodiments, the methods further comprise confirmation of the gene copy number in the test subject. In some embodiments, gene copy number is determined by nucleic acid amplification from a genomic DNA sample isolated from a plurality of diploid cells or a plurality of haploid cells from the subject using a quantitative PCR analysis method (e.g. RT PCR). In such methods, the copy number is determined by comparative Ct against the reference gene.

In some embodiments, one or more oligonucleotide primers in the nucleic acid amplification reaction comprise additional nucleic acid sequences for identification of the amplification products and/or to assist in subsequent manipulation or analysis. For example, in some embodiments one or more oligonucleotide primers in the nucleic acid amplification reaction comprise a unique nucleic acid barcode. In some embodiments, one or more oligonucleotide primers in the nucleic acid amplification reaction comprise an adapter sequence for further amplification, for annealing of a sequencing primer, anchoring of the amplification product to a solid support such as a microbead. In some embodiments, one or more oligonucleotide primers is linked to a solid support such as a microbead.

Data Analysis

Following nucleic acid amplification and detection of the amplified products, the number samples that contain each amplification product, the reference gene amplification product and/or the target gene amplification product is counted. Determination of silent carrier status is determined based on the absence of the target gene amplification product in approximately 50% of the samples that contain a reference gene amplification product. In some embodiments, the ratio of the target gene amplification product to the reference gene amplification product is determined. For example, a ratio of approximately 0.5 for the target gene amplification product to the reference gene amplification product is indicative of a silent carrier.

For individuals that are not silent carriers for SMN1 gene deletion and contain two copies of the SMN1 gene, it is expected that the ratio of the target gene amplification product to the reference gene amplification product is about 1. In some embodiments, samples are selected for further analysis if the ratio of the target gene amplification product to the reference gene amplification product deviates significantly from about 1. In some embodiments, a significant deviation of the ratio of the target gene amplification product to the reference gene amplification product from about 1 indicates that the individual is a silent carrier of the SMN1 null allele. Accordingly, in some embodiments, potential silent carriers are selected if the ratio of the target gene amplification product to the reference gene amplification product is at or below a threshold level. The threshold level can be determined by as appropriate statistical method, for example a single value t-test. In some embodiments, the threshold level is at or below 0.8. In some embodiments, the threshold level is at or below 0.75.

It is understood that the methods provided herein can be performed with the assistance of one or more automated devices or computer modules. For example, procedures for cell seeding, preparation of genomic DNA, dispensing, mixing, removal and/or transfer of reagents to or from reaction vessels, thermocycling for nucleic amplification, detection and quantitation of amplification products, analysis of data, and generation of a report can be automated in part or entirely with the assistance of one or more automated devices or computer modules.

Kits

In some embodiments, provided are kits for the practice of the methods provided herein. In some embodiments, the kits contain one or more reagents for the performance of an amplification reaction for the target gene and a reference gene, and optionally, instructions for use. In some embodiments, the contain reaction vessels, such as microtiter plates, microchips or reaction grid slides and/or suitable containers for the practice of the methods provided herein.

In some embodiments, provided are a microtiter plates containing one or more reagents for the performance of an amplification reaction for the target gene and a reference gene. In some embodiments, the one or more reagents are lyophilized in the microtiter plate. In some embodiments, the lyophilized reagents are reconstituted in an appropriate buffer prior to use. For example, the lyophilized reagents are reconstituted in an appropriate buffer prior to addition of the genomic DNA sample. In some embodiments, the microtiter plate contains a buffering agent. In some embodiments, the buffering agent is selected from the among Tris, MOPS, HEPES, TAPS, Bicine, Tricine, TES, PIPES, IVIES. In some embodiments, the buffering agent is Tris. In some embodiments, the microtiter plate contains a polymerase and a polymerase stabilizing agent, such as a non-ionic detergent, a zwitterionic compound, a cationic ester compound, a polymer, BSA, or a polysaccharide. In some embodiments the microtiter plate contains at least one dNTP. In some embodiments, the microtiter plate contains an oligonucleotide primer set for amplification of the reference gene, the target gene, or both the reference gene and the target gene.

EXAMPLES

Example 1

Method

Frozen human semen specimens (Bioreclamation IVT) were thawed and counted on a TC20 Automated Cell Counter (BioRad). Prior to counting, specimens were incubated for 30 minutes at 37° C., vortexed for a minimum of 30 seconds and diluted 1:1 with TE to ensure a single cell suspension. The resulting counts were then used for the genotyping and single sperm assays. For the SMN1 and SMN2 genotyping assay, DNA from the sperm specimens was extracted using a modified Puregene manual extraction protocol (Qiagen). For the single cell sperm assay, each specimen was individually counted on the TC20 cell counter and diluted to a final concentration of 0.8 cells/µl and 0.4 cells/W.

Sperm lysis was performed in a 96 well PCR plate, to which 1W of the diluted donor sperm specimens was added to 5 W of lysis buffer (0.1 M DDT, 10 mM EDTA, 0.4 M KOH, and 10% Roche recombinant PCR grade proteinase K) for a total volume of 6W/well. Each specimen had 48 replicate wells for the 0.8 cells/µl and 0.4 cells/µl final concentrations. Once the lysis was completed, each plate was prepped for the quantitative PCR assay that was slightly modified from the standard operating procedure to account for a 50W total reaction volume. SMN1 probes and primers (100 µM concentration) were added to TaqMan Fast Advanced Master Mix (Life Technologies) and run as a comparative CT experiment on a ViiA 7 Real Time PCR System for 60 cycles. Specimens were analyzed using ViiA 7 software where SMN1 and a reference control probe positive targets were identified and quantified. Each sperm specimen was diluted to 0.8 and 0.4 cells per well and tested for SMN1 as well as a reference gene to confirm the presence of a single cell. Each well was counted and the values for the reference gene and SMN1 were compared.

For SMN1 and SMN2 amplification, oligonucleotide primers were designed to amplify exon 7 of each gene as described in Curet et al. (2007) *Neurogenetics* 8:271-278. The SMN forward primers distinguish between SMN1 and SMN2 by ending on the nucleotide difference (C/T) at position 6 in exon 7. A mismatch T→G added at the −3 position from the 3' end of both SMN1 and SMN2 forward primers aids in allele specificity.

```
-ex7F-3g:
                                     (SEQ ID NO: 1)
5'-TTCCTTTATTTTCCTTACAGGGTGTC-3'

SMN2-ex7F-3g:
                                     (SEQ ID NO: 2)
5'-TTCCTTTATTTTCCTTACAGGGTGTT-3'

SMN-ex7R
                                     (SEQ ID NO: 3)
5'-GCTGGCAGACTTACTCCTTAATTTAA-3'

CFTR-F
                                     (SEQ ID NO: 4)
5'-TAGGAAGTCACCAAAGCAGTACAGC-3'

CFTR-R
                                     (SEQ ID NO: 5)
5'-AGCTATTCTCATCTGCATTCCAATG-3'
```

Figure 2:
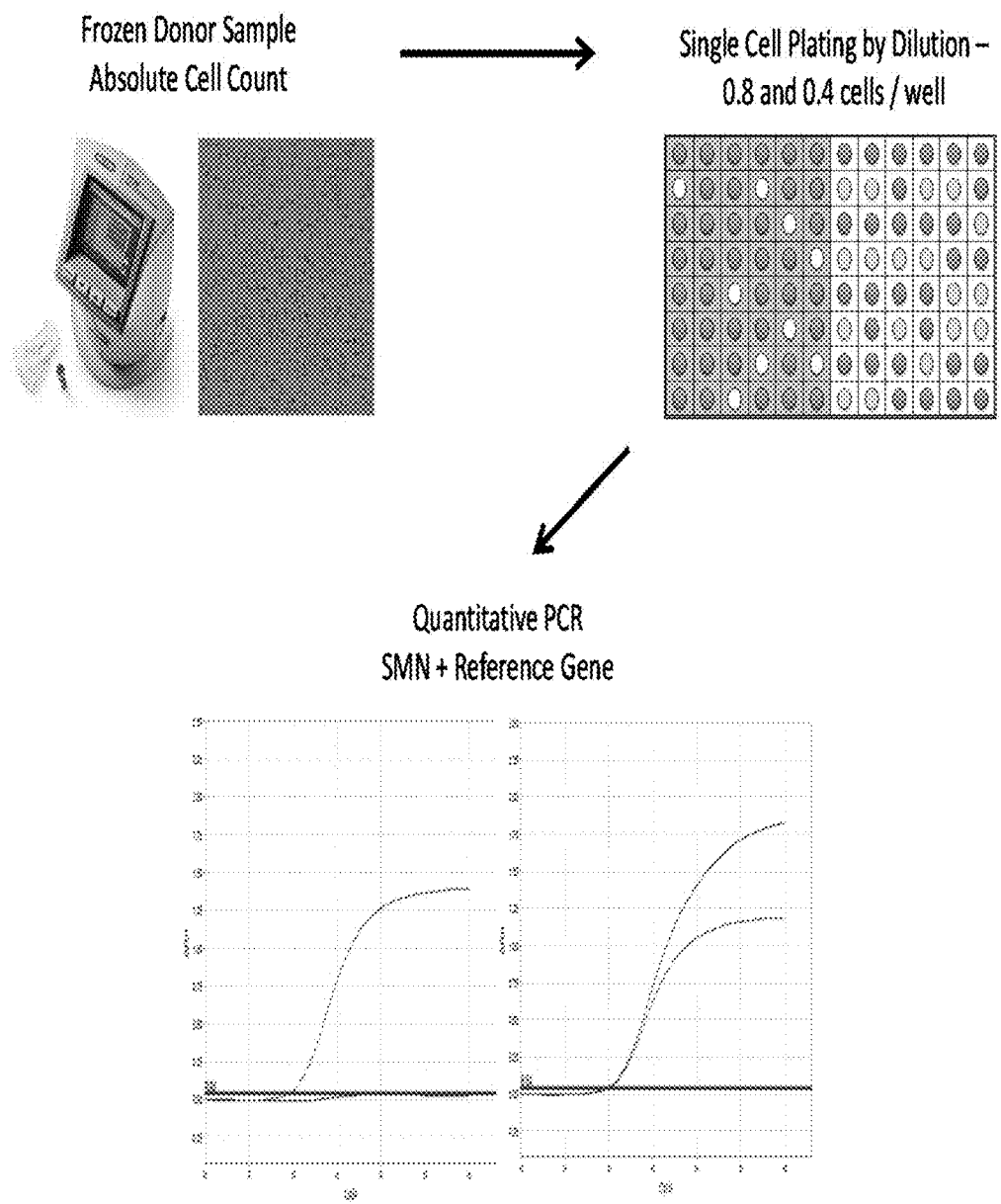
FIG. 2 illustrates an exemplary assay workflow of the single sperm cell qPCR assay.

Results:

A total of 46 African American males were screened for SMA carrier status using the single spermatozoa qPCR assay (FIG. 2). Poor quality specimens, including low counts and contamination, resulted in inconsistent cell counts and significant qPCR reaction failure [7/46 (15%)]. All reliable specimens had at least 2 copies of the SMN1 gene detected by a traditional dosage assay using DNA extracted from the same semen specimen (Data not shown). No traditional SMA carriers (a single copy of SMN1) were identified in this initial data set.

Figure 3:
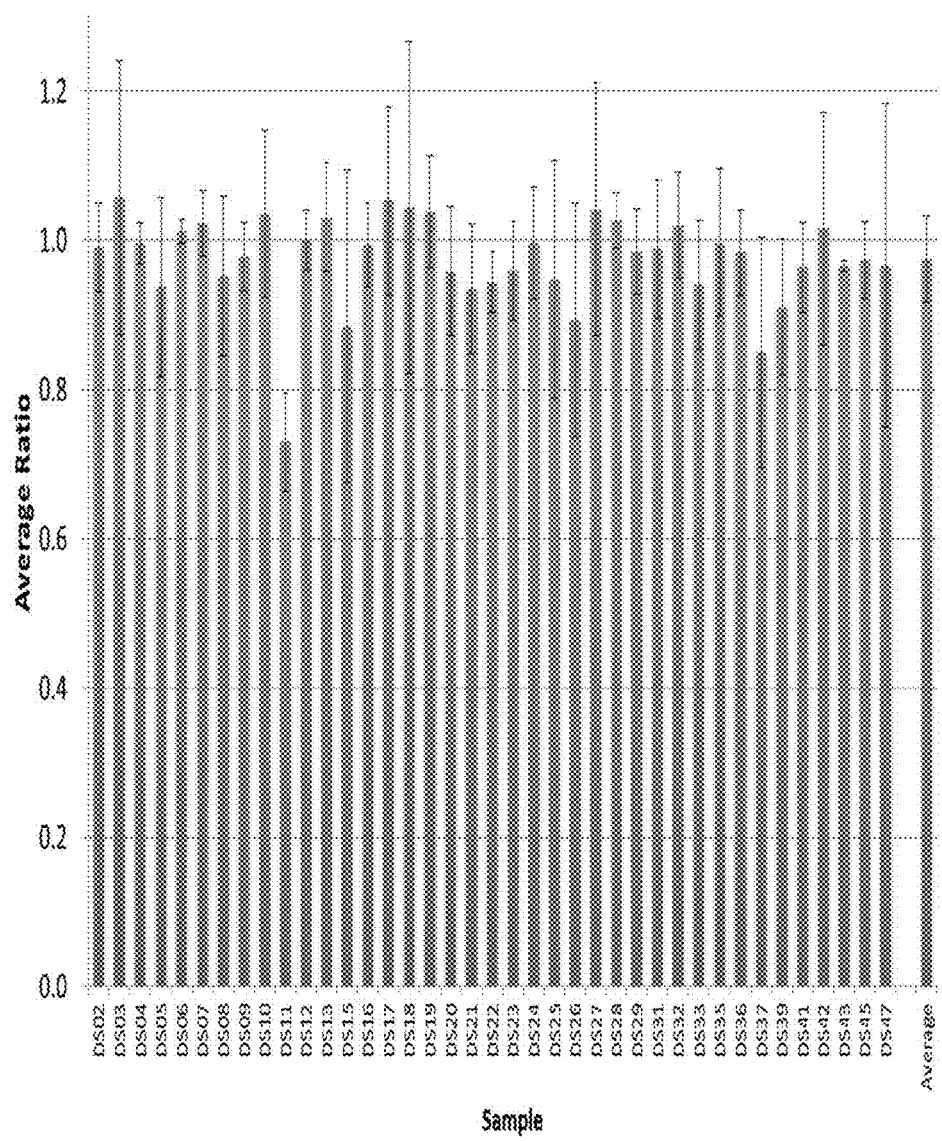
FIG. 3 illustrates data for detecting the SMN1 gene in a single spermatozoa qPCR Assay. The average value of single cell qPCR assay ratio values of SMN1 versus a reference gene and both gene targets versus a reference gene are shown. *P<0.01. Standard deviation of observed values is indicated by error bars.

A single specimen (DS11) statistically deviated (single value t-test p value=0.0014) from the expected SMN1 to reference gene ratio of the average ratio of two copy individuals with a value of 0.729+/−SD 0.66 (FIG. 3). A SMN1 to reference gene ratio of approximately 0.5 suggests a carrier specimen where half of the sperm cells are null for SMN1, with a risk of passing on the disease allele of 50%. An observed genotype of 2 copies of SMN1 and 50% null spermatozoa are indicative of a 2+0 genotype or silent carrier.

Figure 4:
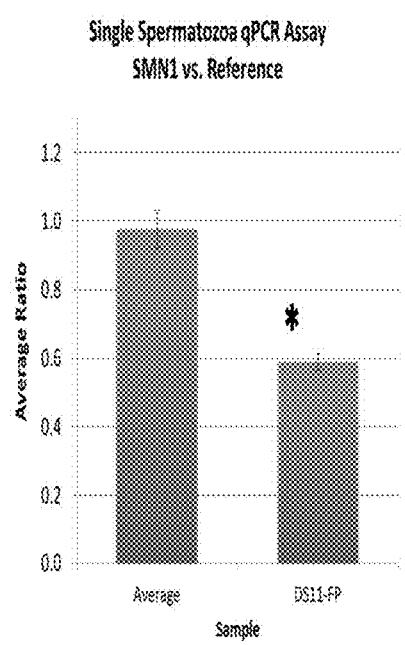
FIG. 4 illustrates resolution of an identified 2+0 Genotype Result. (A) Average value of single cell qPCR assay ratio values of SMN1 versus a reference gene and both gene targets versus a reference gene for specimen DS11. (B) Non-specific sequencing of the SMN1 and SMN2 genes, +6 position of exon 7 c.840C>T highlighted by red box (SEQ ID NOS 6 and 6, respectively, in order of appearance). (C) Specific sequencing of SMN1 qPCR primer and probe sites (SEQ ID NOS 7 and 7, respectively, in order of appearance). *P<0.001. Standard deviation of observed valued indicated by error bars.
Figure 4:
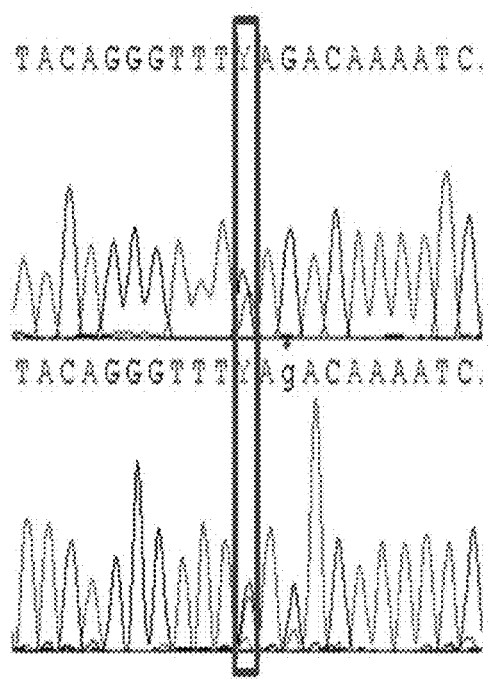
Figure 4:
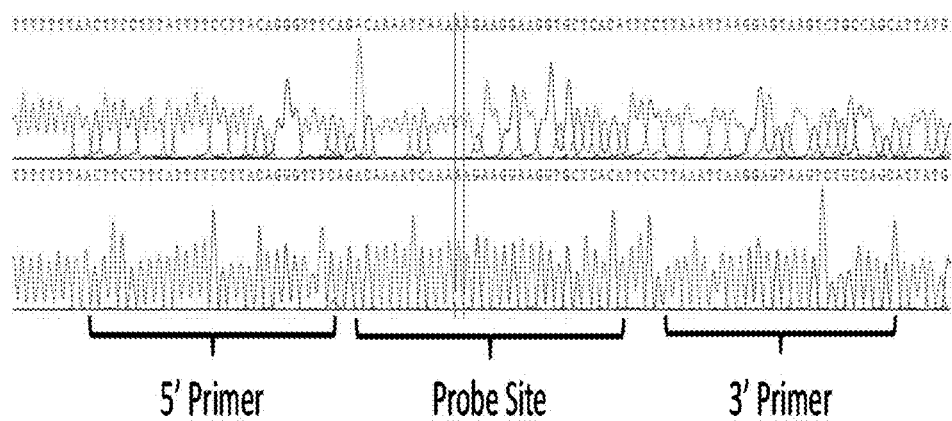

The DS11 specimen was retested by qPCR to determine the dosage of SMN1 and SMN2 genes and with the single cell assay expanded to two full plates at two different dilutions (n=192 total wells). The genotype of specimen DS11 was confirmed to have two copies of SMN1 and two copies of SMN2. The SMN1 to reference gene ratio result was 0.589+/−SD 0.024 (single value t-test p value=$2.2 \times 10^{-4}$), confirming the 2+0 genotype and the initial silent carrier result (FIG. 4A). The specimen was sequenced by Sanger methodologies for SMN1 and non-specific sequencing for SMN1 and the homolog SMN2. Non-specific sequencing of the two homologous genes showed an approximate 50/50 (C/T) ratio at the +6 position of exon 7, indicative of an equal number of copies of the two genes (FIG. 4B). Specific sequencing of the SMN1 gene did not reveal any sequence variants under the qPCR probe or primer sites that may result in allele dropout or decreased probe affinity (FIG. 4C).

The results of this study support the use of a single cell spermatozoa qPCR assay to identify silent SMA carriers in males, eliminating the residual risk of traditional gene dosage methods. In combination with specific sequencing of the SMN1 gene, this novel assay is capable of identifying 100% of all male SMA carriers resulting from deletion or mutation of the SMN1 locus.

The examples and embodiments described herein are for illustrative purposes only and various modifications or changes suggested to persons skilled in the art are to be included within the spirit and purview of this application and scope of the appended claims.

What is claimed is:

1. A method for identifying a subject as a silent carrier of a target gene null allele comprising:
   (a) performing a plurality of quantitative nucleic acid amplification reactions, wherein each nucleic acid amplification reaction comprises (i) a genomic DNA sample obtained from a single haploid cell from the subject, (ii) at least one pair of oligonucleotide primers for amplification of a target region of a target gene, wherein the target region is absent in a target gene null allele, and (iii) at least one pair of oligonucleotide primers for amplification of a target region of a reference gene;
   (b) detecting the presence or absence of the target gene amplification product;
   (c) detecting the presence or absence of the reference gene amplification product;
   (d) determining a ratio of detected target gene amplification product to detected reference gene amplification product; and
   (e) characterizing the subject as a silent carrier of the target gene null allele if the ratio of target gene amplification products to reference gene amplification products is at or below a threshold level between about 0.5 and about 0.8.

2. The method of claim 1, wherein the threshold level is about 0.75.

3. The method of claim 1, wherein the ratio of target gene amplification products to reference gene amplification products in a silent carrier of a target gene null allele is approximately 0.5.

4. The method of claim 1, wherein the haploid cell is a naturally occurring gamete cell or an induced haploid cell.

5. The method of claim 4, wherein the haploid cell is a sperm cell.

6. The method of claim 4, wherein the induced haploid cell is derived from an induced pluripotent stem cell (iPSC).

7. The method of claim 1, wherein the subject is a human subject.

8. The method of claim 1, wherein the reference gene is selected from among CFTR, GAPDH, HMBS, B2M, HPRT1, RPL13A, SDHA, TBP, UBC, YWHAZ, PRDX6, ADD1, HLA-A, RAD9A, ARHGEF7, EIF2B2, PSMD7, BCAT2, and ATP5O.

9. The method of claim 1, wherein the target gene is SMN1.

10. The method of claim 1, wherein the target gene amplification product comprises exon 7 of SMN1 or a portion thereof.

11. The method of claim 1, wherein homozygous deletion of the target gene is associated with a disease or condition.

12. The method of claim 11, wherein the disease or condition is spinal muscular atrophy (SMA).

13. The method of claim 1, wherein at least one oligonucleotide primer for amplification of the target gene is labeled with a detectable moiety.

14. The method of claim 1, wherein at least one oligonucleotide primer for amplification of the reference gene is labeled with a detectable moiety.

15. The method of claim 13 or claim 14, wherein the detectable moiety is a fluorescent moiety.

16. The method of claim 1, wherein the quantitative nucleic acid amplification reaction is quantitative PCR.

17. The method of claim 1, wherein each nucleic acid amplification reaction is performed in a separate well of a multiwell plate.

18. The method of claim 1, wherein each haploid cell is encapsulated in a microdroplet.

19. The method of claim 18, wherein the microdroplets are dispersed in an aqueous-in-oil emulsion.

20. The method of claim 18, wherein the quantitative nucleic acid amplification reaction is droplet digital PCR.

21. The method of claim 1, wherein the target gene amplification product is detected with a labeled nucleic acid probe specific for the target gene amplification product.

22. The method of claim 1, wherein the reference gene amplification product is detected with a labeled nucleic acid probe specific for the reference gene amplification product.

23. The method of claim 1, wherein the method further comprises determining the copy number of the target gene in a diploid cell from the subject.

24. The method of claim 1, wherein the method further comprises generation of a report, wherein the report contains an assessment of the likelihood that the subject is a silent carrier of the target gene null allele.

25. The method of claim 1, wherein the method comprises a step of preparing the genomic DNA from single haploid cells.

26. The method of claim 25, wherein preparing the genomic DNA from single haploid cells comprises:
   (a) sorting single haploid cells into separate reaction vessels at a concentration of one haploid cell per reaction vessel; and
   (b) contacting each sorted cell with a lysis buffer to release the genomic DNA from the cell.

27. The method of claim 26, wherein the lysis buffer comprises an enzyme.

28. The method of claim 27, wherein the lysis buffer comprises proteinase K.

29. The method of claim 26, wherein preparation of the genomic DNA and the nucleic acid amplification reaction are performed in the same reaction vessel.

30. The method of claim 26, wherein preparation of the genomic DNA and the nucleic acid amplification reaction are performed in separate reaction vessels.

31. The method of claim 26, wherein the reaction vessel is a microtiter plate.

32. The method of claim 25, wherein preparing the genomic DNA from single haploid cells comprises:
   (a) encapsulating single haploid cells into aqueous microdroplets at a concentration of one haploid cell per reaction vessel; and
   (b) contacting each single haploid cell within each microdroplet with a lysis buffer to release the genomic DNA from the cell.

* * * * *

SEQUENCE LISTING

```
<160> NUMBER OF SEQ ID NOS: 7

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttcctttatt ttccttacag ggtgtc                                          26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttcctttatt ttccttacag ggtgtt                                          26

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctggcagac ttactcctta atttaa                                          26

<210> SEQ ID NO 4
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 4
taggaagtca ccaaagcagt acagc                                            25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agctattctc atctgcattc caatg                                            25

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tacagggttt yagacaaaat c                                                21

<210> SEQ ID NO 7
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7 ttttttaac ttcctttatt ttccttacag ggtttcagac aaaatcaaaa agaaggaagg       60
tgctcacatt ccttaaatta aggagtaagt ctgccagcat tatg                       104
```